United States Patent [19]

Bacino et al.

[11] 4,326,630
[45] Apr. 27, 1982

[54] SNELLED HOOK PACKAGE AND PACKAGING METHOD

[76] Inventors: Carl J. Bacino, 4482 Fernbrook Rd.; Martin Lustig, 6768 Greengrove St., both of Las Vegas, Nev. 89103

[21] Appl. No.: 150,886

[22] Filed: May 19, 1980

[51] Int. Cl.³ .............................................. A61L 17/02
[52] U.S. Cl. ................................ 206/315 R; 206/63.3
[58] Field of Search ................... 206/315 R, 339, 438, 206/570, 572, 579, 45.11, 63.3, 315; 43/44.83, 44.84, 44.98, 54.5 R, 54.5 A, 57.5 R, 57.5 A

[56] References Cited

U.S. PATENT DOCUMENTS

| | | | |
|---|---|---|---|
| 2,422,870 | 6/1947 | Willis | 206/315 X |
| 3,985,227 | 10/1976 | Thyen et al. | 206/63.3 |
| 4,034,850 | 7/1977 | Mandel et al. | 206/63.3 |
| 4,120,395 | 10/1978 | Mandel et al. | 206/63.3 |
| 4,135,623 | 1/1979 | Thyen | 206/63.3 |
| 4,142,628 | 3/1979 | Marocco et al. | 206/63.3 |

*Primary Examiner*—Steven M. Pollard
*Attorney, Agent, or Firm*—Seiler & Quirk

[57] ABSTRACT

A flat, flexible package for snelled fish hooks is formed from back and front flexible panels sealed around the periphery and containing a series of elongated parallel pockets in which snelled hooks are extended. In a preferred embodiment, leaders of each snelled hook are threaded through the loops of immediately adjacent snelled hooks, such that the hook portion of one snelled hook engages the loop of the adjacent snelled hook upon removal, carrying the loop of the adjacent snelled hook to the exit port in the container.

7 Claims, 4 Drawing Figures

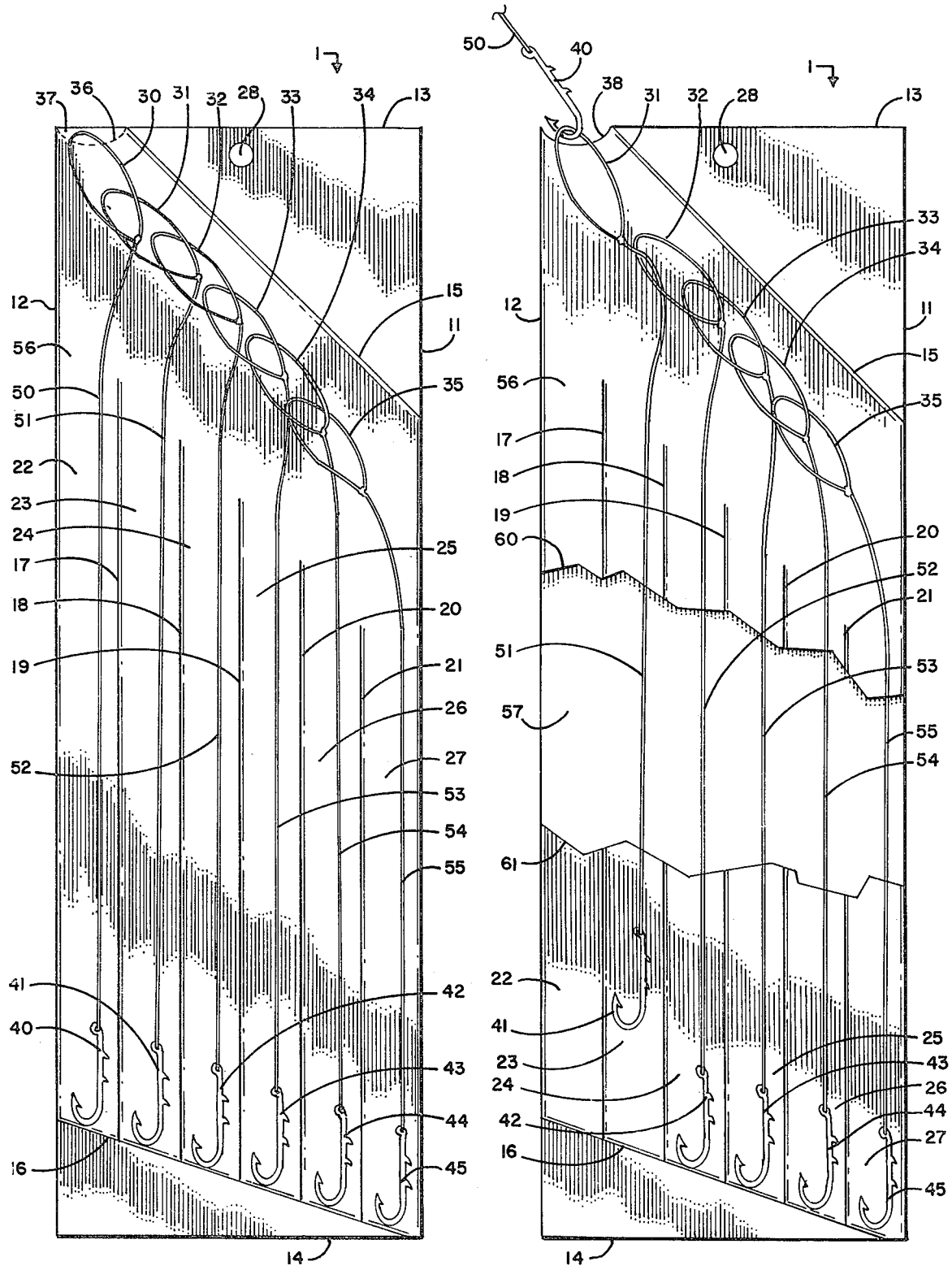

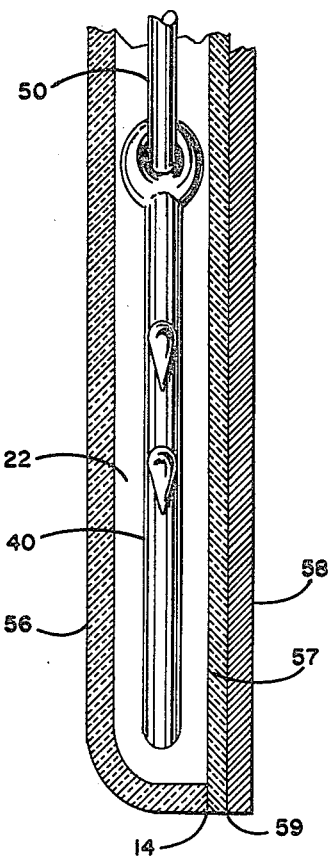
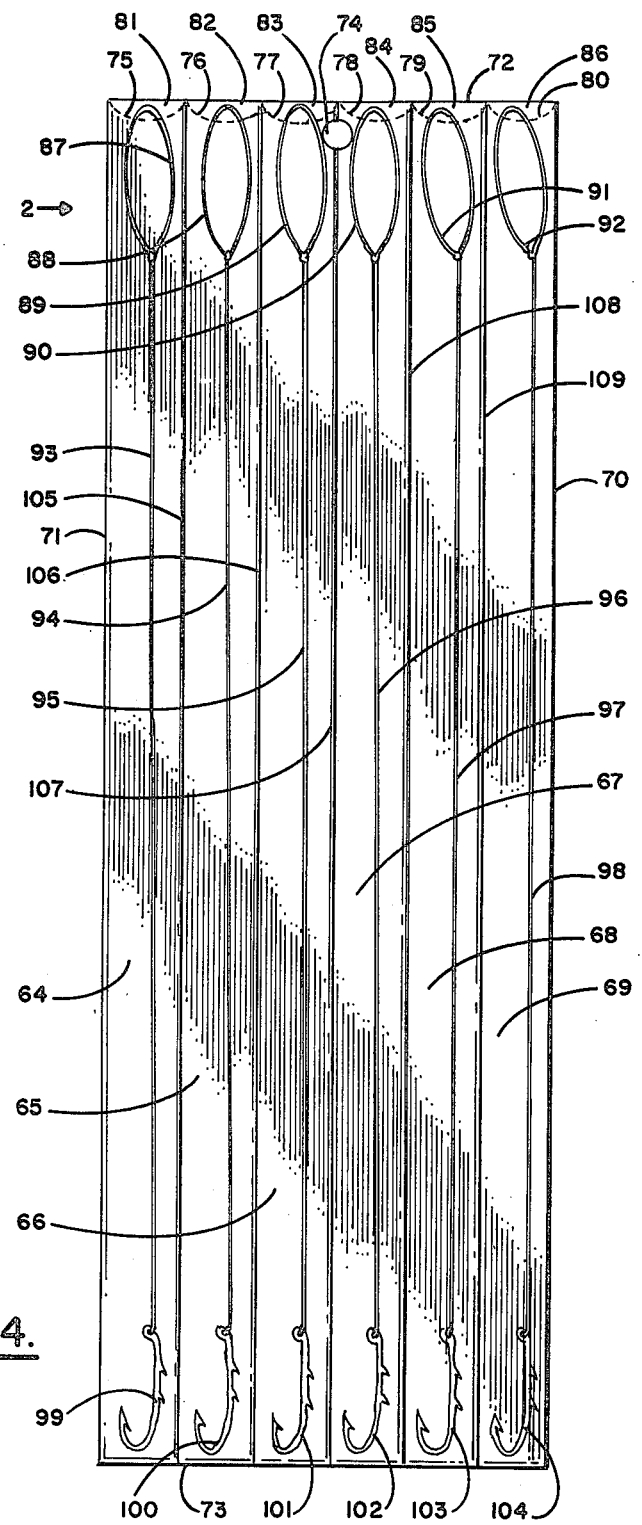
FIGURE 3.
FIGURE 4.

SNELLED HOOK PACKAGE AND PACKAGING METHOD

BACKGROUND OF THE INVENTION

This invention relates to a package and method of packaging snelled fish hooks which permits a fisherman to carry a supply of hooks in his pocket such that the hooks are quickly accessible and can be easily removed from the package without loss, tangling of hooks, and with a minimum amount of handling of the hook.

The problems associated with attaching hooks to fishing lines are familiar ones to most fishermen. In an effort to avoid threading a hook on a fish line under adverse fishing conditions, it is common for the hooks to be sold with a short leader, or "snell", already tied to the hook. The opposite end of the snell terminates in a loop which is much easier to tie to a fishline than the hook. In cold weather, or unstable conditions on a boat, it is a relatively simple matter to tie the line to the loop, without the need for handling the hook or threading the fishline through the relatively narrow metal loop at the end of the hook.

Current methods of packaging snelled hooks are not entirely satisfactory, principally because once the package is opened, the snelled hooks frequently fall out of the package and become entangled, or are left loose in a tackle box where they become a house-keeping problem. Accordingly, there is a need for a means for packaging snelled hooks which permits the hooks to be removed one-at-a-time from the package without the possibility of entanglement with other hooks contained within the package, and with a minimum of handling of the sharp hook.

In the past, numerous packages have been devised for holding snelled hooks. For example, Shannon, U.S. Ser. No. 966,609, discloses a flat metal plate having a roll at one end over which the barb of the hook engages, and having a fastening leaf riveted to the plate to retain the leaders in place. Similar packaging methods for holding a plurality of snelled hooks in parallel position are shown in Cantrell, U.S. Ser. No. 667,676, Crook, U.S. Pat. No. 2,530,292, and Kline, U.S. Pat. No. 3,115,723. The Cantrell patent shows a backing sheet having a spring-bar over which the ends of the hooks are looped, and a front panel which partially covers the snell to maintain it in place. The Crook patent shows a metal container having a plurality of compartments for containing snelled hooks, with the hooks extending forwardly over the front wall to maintain them in position. The Kline patent shows a flexible corrugated cardboard mount for snelled hooks having a slot at one end for retaining the hook members and a piece of scotch tape at the other end to maintain the leader lines attached to the mount. While all of these patents disclose useful methods for carrying hooks, the hooks are not contained within sealed compartments and are therefore likely to get wet or weathered, and it is also necessary to handle the barbed portion of the hooks to remove them from the container, presenting a potential safety hazard.

Another approach to packaging snelled hooks is disclosed in Willis, U.S. Pat. No. 2,422,870, which shows a plurality of snelled hooks attached in hook-to-leader fashion and wound around a spool. When a snelled hook is desired, it is simply unwound from the spool, and the hook portion is disengaged from the adjacent loop of the next leader and chain.

The packaging method and container of the invention are designed to provide the fisherman with easy access to each snelled hook within the package without possibility of entanglement, and with a minimum handling of the hook. It is an object of the invention to provide a snelled hook package in which the hooks are completely enclosed within the package, thereby preventing accidental attachment of the hook barb to clothing, fishing gear, and the like. It is a further object of the invention to provide a package in which the hooks and leaders are substantially sealed, thereby preventing contact with wetness which can rust the hooks. It is yet a further object of the invention to provide a package which is inexpensively manufactured and which meets all safety requirements of the law. These and other objects of the invention will be apparent to one skilled in the art from the following detailed description of the invention.

BRIEF SUMMARY OF THE INVENTION

A snelled hook package comprises an elongate flat sealed container having parallel front and back panels sealed substantially around the periphery of the panels, a plurality of separate parallel compartments within the container, in combination with a plurality of snelled hooks having a fish hook at one end and a loop at the other end, each snelled hook being contained within a separate compartment and aligned lengthwise in the container with all of the loops at the same end in the container, and access means at said end of the container to permit withdrawal of the snelled hook by pulling the loop from the container. In a preferred aspect of the invention, each snell is threaded through the loop of an immediately adjacent snelled hook in the container such that upon withdrawal of a snelled hook from the container, the hook portion of the snelled hook engages the loop portion of the immediately adjacent snelled hook, and draws said loop portion to the opening in the container.

BRIEF DESCRIPTION OF THE DRAWINGS

The invention is best understood with reference to the drawings, in which:

FIG. 1 is a front elevational view of a preferred packaging method for snelled hooks showing each leader threaded through the loop of an adjacent snelled hook;

FIG. 2 is a front elevational view of the embodiment shown in FIG. 1, showing removal of the first snelled hook;

FIG. 3 is a partial side sectional view of a package showing the hook portion of the snelled hook and showing the construction of the package walls; and FIG. 4 depicts another embodiment of the invention in which the snelled hooks are maintained in entirely separate sealed compartments within the container.

DETAILED DESCRIPTION OF A PREFERRED EMBODIMENT

Referring to FIG. 1, container 1 is shown with 6 packaged snelled hooks mounted in adjacent compartments within the container. The snelled hooks comprise leader lines 50, 51, 52, 53, 54, and 55 having hook members 40, 41, 42, 43, 44, and 45 attached at the lower end thereof. The leader lines have loops 30, 31, 32, 33, 34, and 35, respectively, tied at the upper ends thereof. The leaders are generally made from nylon or gut line, and are conventional and commercially available.

The package casing comprises a front panel 56, fabricated from a transparent flexible plastic material such as polyethylene or vinyl, which is attached by heat sealing to a rear panel 57 of like material. Cardboard backing 58 coextensive with rear panel 57 may be secured to the panel at seal 59 by heat sealing or with adhesive, and is used to provide rigidity to the package (if desired) and to provide a surface upon which instructions, advertisements, and the like may easily be printed. Detailed construction of the package is best seen in FIG. 3, which is a partial side section view showing leader 50 attached to hook 40 contained within compartment 22 within the container. Alternative packaging, such as a flexible cylindrical plastic section which is flattened to form front and back panels may be used.

Referring again to FIG. 1, coextensive front and back panels of the container are of substantially the same size and are sealed around edges 11, 12, 13, and 14. The entire internal portion of the container is sealed from the environment. The front and back panels are additionally sealed together along lines 15 and 16 extending angularly across the top and bottom portions of the package, respectively. Accordingly, a sealed internal chamber is formed by seals between the front and back panels along lines 15 and 16, large portions of edges 11 and 12, and a small portion of upper edge 13.

Within the container in the internal chamber are 6 parallel elongated compartments or pockets 22, 23, 24, 25, 26, and 27. These pockets are formed by parallel heat seals 17, 18, 19, 20, and 21, along with edges 11 and 12. Internal heat seals 17 through 21 extend from the bottom of the compartment, defined by heat seal 16, from about ½ to about ¾ of the length of the container. Accordingly, in the embodiment of the invention shown in FIGS. 1 and 2, the pockets are formed in the bottom portion of the internal chamber. Therefore, the looped ends of the snelled hooks are located in a non-compartmentalized section of the container located above the pockets. Other features of the container include a removable tab 37 defined by perforations 36 in the front and back panels located in an upper corner of the container which can be pulled away to open the container and remove the snelled hooks, and a hole 28 at the upper middle portion of the container which may be used to hang the container on a display rack.

The snelled hooks are mounted in the pockets with the leader lines parallel and extending upwardly toward the opening 38 (see FIG. 2) at the top of the container. When the hooks are packaged in the container, each loop beginning with the farthest loop from the opening is successively threaded through the loop of the next adjacent snelled hook. This can be accomplished manually or with a crochet hook by simply threading one loop through the other. For example, in FIG. 1, loop 34 would first be threaded through loop 35, then loop 33 would be threaded through loop 34, loop 32 would be threaded through loop 33, etc.

Removal of the hooks from the container is shown in FIG. 2. To remove the first hook, the user first breaks the seal and removes tab 37 with his thumb, exposing the tip of loop 30. Loop 30 is then grasped between the thumb and forefinger and is pulled away from the container. As the leader is pulled from the container, hook 40 engages loop 31 as it is pulled through the loop, pulling loop 31 toward opening 38 in the container, and reaching the configuration shown in FIG. 2. At this point, the user simply disengages hook 40 from loop 31, and attaches the first snelled hook to his fishing line.

When removal of the second snelled hook is desired, the user simply grasps the exposed portion of loop 31 and pulls it from the container. As the leader is removed, hook 41 engages loop 32 of the next adjacent snelled hook and advances it toward the opening. This process may be repeated until all of the snelled hooks are removed from the container.

The front transparent plastic wall 56 permits the user to see how many hooks are left in the package, and also enables him to view the removal process, which is quite novel. In FIG. 2, cutaway lines 60 and 61 define the top and bottom respectively of the cutaway portion of the front plastic panel, exposing the rear plastic panel 57.

An alternative embodiment of the packaging method of the invention is shown in FIG. 4. Container 2 is generally similar in size and shape to container 1, but has 6 parallel pockets 64, 65, 66, 67, 68, and 69, each extending the entire length of the container. The container is fabricated from front and back plastic panels in the same manner as container 1, and the entire container is sealed via side seams 70 and 71, top seam 72, and bottom seam 73. Each compartment or pocket 64 through 69 has a removable tab 81, 82, 83, 84, 85, and 86 at the end of the compartment, defined by perforations 75, 76, 77, 78, 79, and 80, respectively, thereby providing access means to each compartment for removal of the snelled hook contained therein. As with the first container, removal of the hook is accomplished by pulling away the perforated tab, grasping the loops between the thumb and forefinger, and sliding the loop away from the container.

As illustrated in FIG. 4, hooks 99 through 104 having leaders 93 through 98 attached thereto, and with loops 87 through 92 at the end of the leaders, are shown packaged in channels 64 through 69, respectively. The channels in the container are formed by heat seals 105, 106, 107, 108, and 109, along with edge seals 70 and 71. Container 2 also has a hole 74 at the upper middle portion thereof to receive the arm of a display rack.

The plastics forming technology for manufacturing the container is quite conventional. Heat seals are made by pressing the front and back panels together with a heated blade or surface, causing a softening of the plastic sufficient to melt the two panels together in the area of contact. Loading of the snelled hooks into the containers may either be done manually, by sliding the hooks into the channels prior to sealing the top and bottom edge, or may be done by machine. The machine would follow essentially the same process as the manual packaging, first loading the hooks in the compartments, then intertwining leaders through adjacent loops, and finally sealing the package.

The specific embodiment of the invention described herein shows a package containing six snelled hooks; however, any number of hooks may be included in a package. For convenience, for example, the package may contain from 4 to 12 hooks, but preferably from 5 to 8 hooks.

While the invention has been described with respect to several specific embodiments thereof, it will be readily apparent to those skilled in the art that modifications may be made within the spirit and scope of the invention. Accordingly, the scope of the invention should not be considered limited by the specific description of these embodiments, but rather should be limited only by the following claims.

I claim:

1. A package containing a plurality of snelled fish hooks comprises a completely sealed container having a transparent flexible front panel, a rear panel substantially coextensive with the front panel, a plurality of discrete elongate parallel pockets within the container, access means to remove the snelled fishhooks from the container, each pocket having a snelled fishhook consisting of a leader with a fishhook on one end and a loop on the other end extended therein, and wherein each leader is threaded through the loop of the snelled fishhook in the immediately adjacent pocket.

2. The package of claim 1 having a first snelled hook extended in a first pocket aligned with the loop portion thereof adjacent the access means, and a second snelled hook in a second pocket adjacent the first pocket, the leader portion of the first snelled hook being threaded through the loop of the second snelled hook.

3. The package of claim 2 having a third snelled hook in a third pocket adjacent the second pocket, the leader portion of the second snelled hook being threaded through the loop of the third snelled hook such that when the first snelled hook is removed from the package through the access means, the fishhook portion thereof engages the loop portion of the second snelled hook, drawing it toward the access means, and when the second snelled hook is removed from the package through the access means, the fishhook portion thereof engages the loop portion of the third snelled hook, drawing it toward the access means.

4. The package of claim 1 wherein the interior of the sealed package comprises a chamber having the pockets in a lower portion thereof and the access means adjacent to an upper portion thereof.

5. The package of claim 1 wherein the access means comprises at least one port sealed by a perforated tab.

6. The package of claim 1 wherein each pocket extends substantially the entire length of the package, and the access means comprises a series of ports located at the end of each pocket.

7. The package of claim 1 wherein the container has an inner chamber, said inner chamber being in part separated into a plurality of pockets, each leader being threaded through the loop of the snelled fishhook in the immediately adjacent pocket, the loops being positioned within the chamber above the Pockets, a loop on a leader not having an adjacent leader threaded therethrough being located immediately adjacent to the access means.

* * * * *